United States Patent
McSherry et al.

(10) Patent No.: US 10,433,546 B2
(45) Date of Patent: Oct. 8, 2019

(54) SOLID ANTIMICROBIAL GLUTARALDEHYDE COMPOSITIONS AND THEIR USES

(71) Applicant: Ecolab USA Inc., St. Paul, MN (US)

(72) Inventors: David Daniel McSherry, West St. Paul, MN (US); Benjamin Crew, Eagan, MN (US); Justin Scott Valenstein, Eagan, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/450,257

(22) Filed: Mar. 6, 2017

(65) Prior Publication Data

US 2017/0251665 A1  Sep. 7, 2017

Related U.S. Application Data

(60) Provisional application No. 62/303,787, filed on Mar. 4, 2016.

(51) Int. Cl.
| | | |
|---|---|---|
| *A01N 35/02* | (2006.01) | |
| *A01N 25/10* | (2006.01) | |
| *C09K 8/035* | (2006.01) | |
| *C09K 8/62* | (2006.01) | |
| *E21B 37/06* | (2006.01) | |
| *E21B 43/16* | (2006.01) | |
| *C09K 8/532* | (2006.01) | |
| *C09K 8/54* | (2006.01) | |
| *C23F 11/12* | (2006.01) | |

(52) U.S. Cl.
CPC ............. *A01N 35/02* (2013.01); *A01N 25/10* (2013.01); *C09K 8/035* (2013.01); *C09K 8/532* (2013.01); *C09K 8/54* (2013.01); *C09K 8/62* (2013.01); *C23F 11/122* (2013.01); *E21B 37/06* (2013.01); *E21B 43/16* (2013.01); *C09K 2208/20* (2013.01); *C09K 2208/32* (2013.01)

(58) Field of Classification Search
CPC .... A01N 35/02; A01N 43/16; A01N 2300/00; A01N 25/08; A01N 25/10; A01N 25/22; A01N 25/34; A01N 31/02; A01N 31/06; A01N 43/08; C11D 11/0064; C11D 17/0047; C11D 17/0052; C11D 3/044; C11D 3/08; C11D 3/10; C11D 3/33; C11D 3/3761
See application file for complete search history.

(56) References Cited

U.S. PATENT DOCUMENTS

| | | | |
|---|---|---|---|
| 3,079,985 A | 3/1963 | Boehme et al. | |
| 3,968,250 A | 7/1976 | Boucher | |
| 4,098,859 A | 7/1978 | Cummisford et al. | |
| 4,122,192 A | 10/1978 | Fellows | |
| 4,448,977 A | 5/1984 | Warner et al. | |
| 4,839,373 A | 6/1989 | Ito et al. | |
| 5,158,778 A | 10/1992 | Donovan et al. | |
| 5,480,643 A | 1/1996 | Donovan et al. | |
| 8,276,663 B2 | 10/2012 | Holtsclaw et al. | |
| 8,729,006 B2 * | 5/2014 | Miralles ................. | C11D 3/225 510/245 |
| 2004/0071653 A1 | 4/2004 | Bratescu et al. | |
| 2008/0274940 A1 * | 11/2008 | Tjelta ....................... | C11D 3/10 510/445 |
| 2013/0203845 A1 | 8/2013 | Whiteley et al. | |

FOREIGN PATENT DOCUMENTS

| | | | |
|---|---|---|---|
| DE | 26 05 545 A1 | 9/1976 | |
| DE | 35 17 548 A1 | 11/1986 | |
| EP | 0 046 375 A2 | 2/1982 | |
| EP | 0 251 743 A2 | 1/1988 | |
| GB | 2 017 124 A | 10/1979 | |
| WO | WO95/01724 * | 3/1994 | ............. A01N 35/02 |
| WO | 95/01724 A1 | 1/1995 | |

OTHER PUBLICATIONS

International Search Report and Written Opinion issued for PCT/US2017/020862, dated May 10, 2017, 13 pages.

* cited by examiner

*Primary Examiner* — Audrea B Coniglio
(74) *Attorney, Agent, or Firm* — Stinson LLP

(57) ABSTRACT

A solid glutaraldehyde composition is provided having an increased glass transition temperature. The glutaraldehyde can be used in a method of treating a wellbore or a subterranean formation, by introducing the composition to a wellbore or to an injection line within a wellbore in an amount effective to reduce biodegradation of crude oil, reduce corrosion of metal surfaces from sulfur-reducing bacteria, or to reduce the introduction of bacteria into the formation, reduce microbial contamination of a fluid introduced into the wellbore, or reduce microbial contamination of a pipeline.

18 Claims, No Drawings

SOLID ANTIMICROBIAL GLUTARALDEHYDE COMPOSITIONS AND THEIR USES

CROSS REFERENCE TO RELATED APPLICATIONS

This application claims the benefit of U.S. Provisional Patent Application Ser. No. 62/303,787 filed on Mar. 4, 2016, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

The present invention generally relates to improved solid glutaraldehyde compositions for use as an antimicrobial source of glutaraldehyde in the oil and natural gas industry and any environment which might exceed 50° C.

BACKGROUND OF THE INVENTION

Microbiological contamination of an oil or natural gas environment can lead to degradation of hydrocarbons, and increased sulfur content and viscosity. These changes adversely impact extraction and processing equipment by causing corrosion and production of hydrogen sulfide and other undesirable substances. Antimicrobial additives have been used to control the growth of microorganisms in such environments. While glutaraldehyde, Bronopol and THTP have been used extensively for controlling these organisms in subterranean formations, only Bronopol and THTP have been available in solid rod form to allow well delivery modes.

Solid glutaraldehyde derived by forming a hemiacetal derivative with sucrose is described in U.S. Pat. No. 5,158,778. While the existing solid glutaraldehyde composition is an effective antimicrobial, the composition is a true glass which, though hard and brittle, "flows" like an extremely viscous liquid. The glass transition temperature of the solid glutaraldehyde is about 45° C., which is less than desirable for use in many high temperature environments such as oil fields. More specifically, such solid glutaraldehyde will not maintain it shape when exposed to temperatures of about 50° C. for more than several hours. Since a ball valve access port on a well has an internal diameter ranging from 1 to 1-¼ inch, even minor deforming of the rod can prevent insertion through the valve. Additionally, when the rods are exposed to such temperatures, they tend to fuse to one another again prohibiting insertion through the valve. When a conventional rod is inserted into the ball valve, it typically falls one to two miles down the annulus cavity of the well. If it hits the sides of the annulus, and it is fragile, it will form a surface coating resulting in loss of material and requiring a costly water rinse of the annulus It would therefore be useful to provide solid glutaraldehyde compositions of greater strength to better withstand normal handling without breakage, and to resist deformation or fusing of rods so that the rods can fall through the annulus cavity of a well with minimal or no loss of material from collisions with the annulus surface.

BRIEF SUMMARY OF THE INVENTION

A solid antimicrobial composition is provided. The composition comprises from about 2 to about 70 wt. % glutaraldehyde; from about 10 to about 79.9 wt. % sucrose; from about 0.1 to about 20 wt. % polyacrylic acid; and less than 10 wt. % water. The glass transition temperature of the composition is greater than the glass transition temperature of the same composition devoid of polyacrylic acid, or the composition is derived from a molten blend comprising the glutaraldehyde, sucrose and polyacrylic acid.

A method of making the solid antimicrobial composition is also provided, the method comprising: adding the sucrose to aqueous glutaraldehyde to form a mixture; heating the mixture to dissolve the sucrose to form a clear homogeneous solution; adding the polyacrylic acid to the mixture before or during heating of the mixture; and removing volatiles from the solution to form the solid antimicrobial composition.

A method of preserving, sanitizing, disinfecting or sterilizing a contaminated surface or material is provided, the method comprising: exposing the contaminated surface or material to an effective amount of the composition.

Also provided is a method of treating a wellbore or a subterranean formation. The method comprises introducing the composition to a wellbore or to an injection line within a wellbore in an amount effective to reduce biodegradation of crude oil, reduce corrosion of metal surfaces from sulfur-reducing bacteria, or to reduce the introduction of bacteria into the formation, reduce microbial contamination of a fluid introduced into the wellbore, or reduce microbial contamination of a pipeline.

Other objects and features will be in part apparent and in part pointed out hereinafter.

BRIEF DESCRIPTION OF THE SEVERAL VIEWS OF THE DRAWING

Not applicable.

DETAILED DESCRIPTION OF THE INVENTION

A solid antimicrobial composition is provided. The composition comprises from about 2 to about 70 wt. % glutaraldehyde; from about 10 to about 79.9 wt. % sucrose; from about 0.1 to about 20 wt. % polyacrylic acid; and less than 10 wt. % water. The glass transition temperature of the composition is greater than the glass transition temperature of the same composition devoid of polyacrylic acid, or the composition is derived from a molten blend comprising the glutaraldehyde, sucrose and polyacrylic acid.

Preferably, the glass transition temperature of the composition is greater than the glass transition temperature of the same composition devoid of polyacrylic acid. For example, the glass transition temperature (Tg) range of the composition is about 5 to about 10° C. greater than the glass transition temperature of the same composition devoid of polyacrylic acid. The Tg range is greatly broadened by the addition of polyacrylic acid. For example, the Tg range in general is broadened about 400% from a Tg of about 2° C. to a Tg of about 8° C.

Preferably, the composition is derived from a molten blend comprising the glutaraldehyde, sucrose and polyacrylic acid.

The glass transition temperature of the composition is also impacted by its glutaraldehyde content. If the composition contains more than about 70 wt. % glutaraldehyde, its glass transition temperature may be too low, which can result in breakage of the composition during normal handling, resulting in a loss of activity over the treatment period due to a reduction in the amount of glutaraldehyde successfully delivered to the subterranean formation if the composition is used in treating a wellbore or subterranean formation.

The water content of the composition should not exceed about 10 wt. % or the melting point of the composition may be depressed. A water content of about 1 to 2 wt. % is preferred.

The composition can comprise from about 20 to about 70 wt. % glutaraldehyde; from about 10 to about 79.9 wt. % sucrose; from about 0.1 to about 10 wt. % polyacrylic acid; and less than 10 wt. % water.

The composition can comprise from about 30 to about 60 wt. % glutaraldehyde; from about 33 to about 68 wt. % sucrose; from about 2 to about 5 wt. % polyacrylic acid; and less than 5 wt. % water. Preferably, the composition comprises from about 40 to about 55 wt. % glutaraldehyde; from about 40 to about 55 wt. % sucrose; from about 2 to about 3 wt. % polyacrylic acid; and less than 3 wt. % water.

The polyacrylic acid selected for the composition is soluble in an aqueous glutaraldehyde solution. Suitable polyacrylic acids include, but are not limited to, Aquatreat® AR-6 polyacrylic acid (100,000 Dalton molecular weight; 24-26% solids) commercially available from Akzo Nobel Surface Chemistry LLC (Chicago, Ill.) and Sokalan PA 80 S polyacrylic acid (100,000 Dalton molecular weight; 35% solids) and Sokalan PA 110S polyacrylic acid (up to 250,000 Dalton molecular weight, 35% solids) commercially available from BASF (Florham Park, N.J.). For purposes of this invention, a compound is "soluble" in the aqueous glutaraldehyde solution if the solid loses mass as a function of time exposed to water and leaves less than 1% of that mass dispersed in the solution.

Preferably, the polyacrylic acid has a molecular weight greater than 50,000 Daltons, more preferably from about 75,000 to about 250,000 Daltons, from about 85,000 to about 250,000 Daltons, or about 100,000 to about 250,000 Daltons.

The composition can include a monovalent or polyvalent metal ion. It has been discovered that the presence of the metal ions decreases the dissolution rate so that the glutaraldehyde composition provides a longer effective treatment period as compared to the same composition which does not include the monovalent or polyvalent metal ions. Also, the presence of the metal ions increases the glass transition temperature of the solid glutaraldehyde composition as compared to the same composition which does not include the monovalent or polyvalent metal ions. The monovalent metal ion can be sodium or potassium. The polyvalent metal ion can be, for example, magnesium, calcium, zinc, or a combination thereof.

The composition can be in the form of a rod, a powder, a block, pastilles or granules, or a pressed or extruded solid made from powder, pastilles or granules.

The composition is not a physical blend (i.e., mechanical blend) of a solid polyacrylic acid and a solid hemiacetal composition containing glutaraldehyde and sucrose as described, for example, in U.S. Pat. No. 5,158,778. A physical blend does not involve interaction of the solid polyacrylic acid and the solid hemiacetal composition. The composition described herein involves interaction of the solid polyacrylic acid and the solid hemiacetal composition.

Preferably, the composition does not contain a silica.

A method of making the solid antimicrobial composition as described herein is also provided. The method comprises adding the sucrose to aqueous glutaraldehyde to form a mixture; heating the mixture to dissolve the sucrose to form a clear homogeneous solution; adding the polyacrylic acid to the mixture before or during heating of the mixture; and removing volatiles from the solution to form the solid antimicrobial composition.

Optionally, volatiles can be removed from the clear homogenous solution before addition of the polyacrylic acid. Since polyacrylic acid is frequently accompanied by 2-3 parts water, such additional evaporation of the volatiles further elevates the Tg.

A source of a monovalent or polyvalent metal ion, such as a monovalent or polyvalent metal salt (e.g., magnesium sulfate, calcium sulfate, calcium acetate or calcium nitrate), can be added to the mixture or the homogeneous solution. Preferably, from about 0.01 to about 10 wt. % of the source of the monovalent or polyvalent metal ion is added to the mixture or the homogeneous solution, based on the total weight of the homogenous solution.

The composition can be made, for example, by adding sucrose (99% purity) to aqueous glutaraldehyde (50% glutaraldehyde in water) to form a mixture; heating the mixture to dissolve the sucrose to form a clear homogeneous solution; adding the polyacrylic acid (e.g., Aquatreat® AR-6; 24-26% solids) to the mixture before or during heating of the mixture; and removing volatiles from the solution by rotary evaporation (at reduced pressure) to form the solid antimicrobial composition.

A method of preserving, sanitizing, disinfecting or sterilizing a contaminated surface or material is also provided. The method comprises exposing the contaminated surface or material to an effective amount of the composition as described herein.

The contaminated surface or material can be at least a portion of a cooling water system, a heating, ventilation or air conditioning system, medical equipment, dental equipment, food and beverage handling equipment, a food or beverage container, a textile, clothing, a mining operation, a hydraulic fracturing operation, a gas storage system, an oil storage system, a phase separation system or tank, a pipeline pigging operation, an oil well, a crude oil, a natural gas stream, a refined oil, an injection fluid, a pipeline, a drilling fluid, a fracturing fluid, produced water or animal hooves or teats. For example, the composition can be used to treat livestock hooves or teats by sanitizing the hooves or teats or by assisting healing of the infected surface.

A method of treating a wellbore or a subterranean formation is also provided. The method comprises introducing the composition as described herein to a wellbore or to an injection line within a wellbore in an amount effective to reduce biodegradation of crude oil, reduce corrosion of metal surfaces from sulfur-reducing bacteria, to reduce the introduction of bacteria into the formation, reduce microbial contamination of a fluid introduced into the wellbore, or reduce microbial contamination of a pipeline.

The composition can be introduced at a dosage rate of about 10 to about 10,000 ppm as active glutaraldehyde, more preferably at a dosage rate of about 30 to about 6,000 ppm as active glutaraldehyde, or most preferably at a dosage rate of about 30 to about 3,000 ppm as active glutaraldehyde.

The compositions can be used in various ways, preferably in solid soluble block form, including use as hard surface disinfectants, sanitizers such as those used in the food and beverage industry, cold sterilants such as those used in the health care industry, or antimicrobials such as used in pest elimination, textile care and laundry, paper and mining industries.

Having described the invention in detail, it will be apparent that modifications and variations are possible without departing from the scope of the invention defined in the appended claims.

EXAMPLES

The following non-limiting examples are provided to further illustrate the present invention.

Example 1

A conventional solid glutaraldehyde composition was made by adding 1.4 grams of deionized water to 70.3 grams of 50% aqueous glutaraldehyde, followed by addition of 28.3 grams of sucrose (99% purity). The solution was heated on a steam bath until all of the sucrose was dissolved, forming a clear homogeneous solution. The reaction solution was stripped of its volatiles on a rotary evaporator at 80° C. The resulting product was a hard, clear, crushable foam. The glass transition temperature of the product was 50° C. Its viscosity at 80° C. was 1,000 cP, and its glutaraldehyde activity was 54% using Ecolab QA™ 488 (Ecolab variant of a generic MBTH-aldehyde hydrazone method).

Example 2

A solid glutaraldehyde composition of the invention was made by adding 1.5 grams of deionized water to 67.2 grams of 50% aqueous glutaraldehyde, followed by addition of 27.1 grams of sucrose (99% purity). The solution was heated on the rotary evaporator's water bath until all of the sucrose was dissolved, forming a clear homogeneous solution. Polyacrylic acid (Aquatreat® AR-6 polyacrylic acid; 24-26% solids; 100,000 MW) in an amount of 4.2 grams (4.2 wt. %) was added to the mixture, before heating of the mixture, and was dissolved in the clear homogeneous solution. The reaction solution was stripped of its volatiles on a rotary evaporator at 80°-90° C. The resulting product was a hard, clear, crushable foam. The glass transition temperature of the product was 68° C. as determined using differential scanning calorimetry. Its viscosity at 80° C. was 30,000 cP, and its glutaraldehyde activity was 46% as determined using Ecolab QA™ 488. The final composition of the product comprised 47.9 wt. % glutaraldehyde, 46.4 wt. % sucrose, 2.2 wt. % polyacrylic acid and 2.3 wt. % water.

Example 3

Another solid glutaraldehyde composition of the invention was made by adding 108.1 grams of 50% aqueous glutaraldehyde, followed by addition of 41.6 grams of sucrose (99% purity). The solution was heated on a rotary evaporator until all of the sucrose was dissolved, forming a clear homogeneous solution. Polyacrylic acid (Sokalan PA 110 S polyacrylic acid; 35% solids; 250,000 MW) in an amount of 0.33 grams was added to the mixture, after removing most of the volatile components of the sucrose-glutaraldehyde solution, and was dissolved in the clear homogeneous solution. Magnesium sulfate in an amount of 0.68 grams was added to the mixture before heating of the mixture. The reaction solution was stripped of its volatiles on a rotary evaporator at 80° C. The resulting product was a hard, translucent white, crushable foam. The glass transition temperature range of the product was 55.5-73.7° C. as determined using differential scanning calorimetry. Its glutaraldehyde activity was 42.9% as determined using Ecolab QA™ 488. The final composition of the product comprised 42.9 wt. % glutaraldehyde, 46.1 wt. % sucrose, 0.13 wt. % polyacrylic acid, 1.4 wt. % water, and 0.75 wt. % magnesium sulfate.

In comparing the conventional solid glutaraldehyde of Example 1 to the solid glutaraldehyde of the invention as in Examples 2 and 3, the addition of polyacrylic acid and optionally a source of a divalent metal ion (magnesium) increased the glass transition temperature significantly as compared to the solid glutaraldehyde of Example 1. The compositions of Examples 2 and 3 exhibited greater strength than the composition of Example 1.

In an improvement on Examples 1 and 2 it was discovered that if the addition of the polyacrylic acid was made after removing most of the volatile components of the sucrose—glutaraldehyde solution, the processing time could be shortened and a lower moisture residue was achieved thus maximizing the Tg. In addition it was discovered that using a modulated differential scanning calorimetric technique allowed for the determination of a Tg range. Finally it was found that if the product melting points were measured at a consistent heating rate (10° C./minute) a single point value (measured with a Mettler FP 62 Melting Point Apparatus) was obtained which allows for convenient comparisons between samples. Additional solid glutaraldehyde compositions were made as described in the above examples. The final compositions of the solid glutaraldehyde products are shown in Table 1 wherein Glut is glutaraldehyde, PAA is polyacrylic acid and MgSO$_4$ is magnesium sulfate.

TABLE 1

| Composition No. | Actual Glut (wt. %) | Residual Water (wt. %, KF) | PAA (wt. %) | MgSO$_4$ (wt. %) | Tg Low (° C.) | Tg High (° C.) |
| --- | --- | --- | --- | --- | --- | --- |
| 1 | 42.9 | 1.4 | 0.13 | 0.75 | 55.5 | 73.7 |
| 2 | 42.9 | 2.6 | 1.3 | 0.25 | 51.2 | 65.7 |
| 3 | 40.6 | 1.1 | 1.3 | 0.76 | 57.0 | 74.7 |
| 4 | 39.9 | 1.1 | 1.3 | 1.3 | 52.5 | 73.0 |
| 5 | 40.1 | 3.8 | 2.5 | 0.75 | 50.0 | 65.0 |

The compositions provided in Table 1 were then tested in an overnight flow test at 50° C. The overnight flow test at 50° C. was conducted by placing a small amount of the solid glutaraldehyde composition in a container. Then the container was placed in a 50° C. oven and inverted. The container and its contents remained inverted overnight. In the morning, observations were made as to the state of the solid glutaraldehyde in the container. If the solid glutaraldehyde deformed (pieces fused together, sample slowly flowed down the side of the container, etc.), the solid glutaraldehyde composition did not pass the overnight flow test at 50° C. MP (melting points) were measured using capillary tube samples in a Mettler FP62 Melting Point, at a heating ramp rate of 45° C., beginning at 45° C. The solid glutaraldehyde compositions provided in Table 1 all passed the overnight flow test at 50° C.

TABLE 2

| Sample No. | Wt. % volatiles removed | Melting Point (° C.) | Tg low (° C.) | Tg high (° C.) | Actual Glut. (%) | Residual H2O (%, KF) | Overnight Flow Test at 50° C. |
|---|---|---|---|---|---|---|---|
| 1 | 46% | 73 | 58 | 62 | 42 | 1.4 | passed |
| 2 | 45% | 66 | 53 | 57 | 42 | 2.5 | passed |
| 3 | 48% | 75 | 59 | 65 | 39 | 1.7 | passed |
| 4 | 46% | 74 | 56 | 64 | 40 | 1.7 | passed |
| 5 | 45% | 64 | 54 | 56 | 46 | 2.3 | almost passed |
| 6 | 41% | 70 | 56 | 59 | 45 | 1.7 | passed |
| 7 | 43% | 66 | 52 | 55 | 46 | 2.0 | almost passed |
| 8 | 42% | 64 | 52 | 55 | 48 | 1.9 | almost passed |
| 9 | 41% | 72 | 59 | 61 | 43 | 1.7 | passed |
| 10 | 41% | 72 | 59 | 62 | 42 | 1.6 | passed |
| Average for passed | 44% | 72 | 57 | 61 | 42 | 1.8 | passed |
| Average for almost passed | 43% | 64 | 53 | 55 | 46 | 2.1 | almost passed |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A solid antimicrobial composition comprising:
   from 2 to 70 wt. % glutaraldehyde;
   from 10 to 79.9 wt. % sucrose;
   from 0.1 to 20 wt. % polyacrylic acid; and
   less than 10 wt. % water,
   wherein the composition is derived from a molten blend comprising the glutaraldehyde, sucrose and polyacrylic acid; and the glass transition temperature of the composition is at least 5° C. greater than the glass transition temperature of the same composition devoid of polyacrylic acid.

2. The composition of claim 1, wherein the glass transition temperature of the composition is 5 to 10° C. greater than the glass transition temperature of the same composition devoid of polyacrylic acid.

3. The composition of claim 1, comprising from 20 to 70 wt. % glutaraldehyde; from 10 to 79.9 wt.% sucrose; from 0.1 to 10 wt. % polyacrylic acid; and less than 10 wt. % water.

4. The composition of claim 1, comprising from 30 to 60wt. % glutaraldehyde; from 33 to 68 wt. % sucrose; from 2 to 5 wt. % polyacrylic acid; and less than 5 wt. % water.

5. The composition of claim 1, wherein the polyacrylic acid has a molecular weight greater than 50,000 Daltons.

6. The composition of claim 5, wherein the polyacrylic acid has a molecular weight ranging from 75,000 to 250,000 Daltons.

7. The composition of claim 1, wherein the composition is in the form of a rod, a powder, a block, pastilles or granules, or a pressed or extruded solid made from powder, pastilles or granules.

8. The composition of claim 1, wherein the composition does not contain a silica.

9. The composition of claim 1, wherein the polyacrylic acid is soluble in an aqueous glutaraldehyde solution.

10. The composition of claim 1, further comprising a monovalent or polyvalent metal.

11. The composition of claim 10, wherein the polyvalent metal comprises magnesium, calcium, zinc, or a combination thereof.

12. A method of making the solid antimicrobial composition of claim 1, the method comprising:
   adding the sucrose to aqueous glutaraldehyde to form a mixture;
   heating the mixture to dissolve the sucrose to form a clear homogeneous solution;
   adding the polyacrylic acid to the mixture before or during heating of the mixture; and
   removing volatiles from the solution to form the solid antimicrobial composition.

13. The method of claim 12, further comprising adding to the mixture or the homogeneous solution from 0.01 to 10 wt. % of a source of a polyvalent metal ion, based on the total weight of the homogenous solution.

14. The method of claim 13, wherein the polyvalent metal ion comprises magnesium or calcium.

15. A method of preserving, sanitizing, disinfecting or sterilizing a contaminated surface or material, the method comprising:
   exposing the contaminated surface or material to an effective amount of the composition of claim 1.

16. The method of claim 15, wherein the contaminated surface or material is at least a portion of a cooling water system, a heating, ventilation or air conditioning system, medical equipment, dental equipment, food and beverage handling equipment, a food or beverage container, a textile, clothing, a mining operation, a hydraulic fracturing operation, a gas storage system, an oil storage system, a phase separation system or tank, a pipeline pigging operation, an oil well, a crude oil, a natural gas stream, a refined oil, an injection fluid, a pipeline, a drilling fluid, a fracturing fluid, produced water or livestock hooves or teats.

17. A method of treating a wellbore or a subterranean formation, the method comprising:
   introducing the composition of claim 1 to a wellbore or to an injection line within a wellbore in an amount effective to reduce biodegradation of crude oil, reduce corrosion of metal surfaces from sulfur-reducing bacteria, or to reduce the introduction of bacteria into the formation, reduce microbial contamination of a fluid introduced into the wellbore, or reduce microbial contamination of a pipeline.

18. The method of claim 17, wherein the composition is introduced at a dosage rate of 10 to 10,000 ppm as active glutaraldehyde.

* * * * *